(12) United States Patent
Rheinheimer et al.

(10) Patent No.: US 6,881,742 B1
(45) Date of Patent: Apr. 19, 2005

(54) BENZYL AMIDOXIME DERIVATIVES, INTERMEDIATE PRODUCTS AND METHOD FOR THEIR PRODUCTION AND USE AS FUNGICIDES

(75) Inventors: Joachim Rheinheimer, Ludwigshafen (DE); Karl Eicken, Wachenheim (DE); Ingo Rose, Mannheim (DE); Thomas Grote, Wachenheim (DE); Eberhard Ammermann, Heppenheim (DE); John-Bryan Speakman, Bobenheim (DE); Siegfried Strathmann, Limburgerhof (DE); Gisela Lorenz, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 5 days.

(21) Appl. No.: 10/089,148

(22) PCT Filed: Oct. 5, 2000

(86) PCT No.: PCT/EP00/09744
§ 371 (c)(1),
(2), (4) Date: Mar. 27, 2002

(87) PCT Pub. No.: WO01/25187
PCT Pub. Date: Apr. 12, 2001

(30) Foreign Application Priority Data

Oct. 6, 1999 (DE) .......................... 199 48 266

(51) Int. Cl.$^7$ .......... A01N 43/10; A01N 43/36; A01N 43/40; A01N 43/50; A01N 33/08; C07D 213/44; C07D 213/78; C07D 231/14; C07D 239/28; C07D 277/30

(52) U.S. Cl. ............... 514/336; 546/275.4; 546/280.1; 546/334; 548/370.1; 564/229; 514/336; 514/340; 514/350; 514/406; 514/432; 514/633

(58) Field of Search ............... 546/334, 275.4, 546/280.1; 548/370.1; 549/28; 564/229; 514/336, 340, 350, 406, 432, 633

(56) References Cited

U.S. PATENT DOCUMENTS 3,991,210 A   11/1976 Shea .................. 424/326

FOREIGN PATENT DOCUMENTS

| GB | 285080 | | 4/1929 | | |
|---|---|---|---|---|---|
| GB | 876079 | | 8/1961 | | |
| JP | 10-95771 | * | 4/1998 | ......... | C07D/213/78 |
| JP | 10-095771 | | 4/1998 | | |
| JP | 10/095771 | * | 4/1998 | ......... | C07D/213/78 |

OTHER PUBLICATIONS

Aroyan et al. "Synthesis of some amines, amidoximes, and derivatives of guanidine" Izv. Akad. nauk Arm. SSR, Khim. Nauki vol. 17 No. 5 (1964) pp. 543–548.

Suzue et al. "Synthetic Antimicrobials II Synthesis of Pyrazolo[1,5-α]pyridine Derivatives (1)" Chem. Pharm. Bull. vol. 21, (1973) pp. 2146–2160.

Oussad et al. "Improved Synthesis of Oxadiazoles Under Microwave Irradiation" Synthetic Communications vol. 25 No. 10 (1995) pp. 1451–1459.

* cited by examiner

*Primary Examiner*—Joseph K. McKane
*Assistant Examiner*—Janet L Coppins
(74) *Attorney, Agent, or Firm*—Novak Druce & Quigg, LLP

(57) ABSTRACT

Novel benzamidoxime derivatives, processes and intermediates for their preparation and their use as fungicides are described.

In the context of the present invention, benzamidoxime derivatives are compounds of the formula I

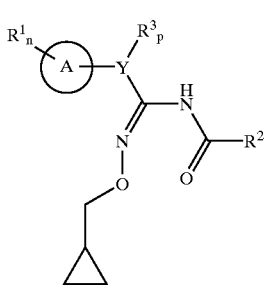

I where:
A is an aryl or hetaryl radical;
Y is a straight-chain or branched $C_1$–$C_4$-alkylene group, where one carbon can be replaced by oxygen, nitrogen or sulfur or by a cyclopropyl group;
$R_n^1$ are one to five identical or different radicals from the group consisting of: hydrogen, halogen, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkoxyalkoxy;
$R^2$ is unsubstituted or substituted phenyl-$C_1$–$C_6$-alkyl, thienyl-$C_1$–$C_4$-alkyl, or pyrazolyl-$C_1$–$C_4$-alkyl,
$R_p^3$ are one to five identical or different radicals from the group consisting of: hydrogen, halogen, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkoxyalkoxy, $C_1$–$C_6$-alkylcarbonyl;
n is 0–5;
p is, depending on the number of free valencies, 0–4.

16 Claims, No Drawings

BENZYL AMIDOXIME DERIVATIVES, INTERMEDIATE PRODUCTS AND METHOD FOR THEIR PRODUCTION AND USE AS FUNGICIDES

The present invention relates to novel benzamidoxime derivatives, to processes and intermediates for their preparation an to their use as fungicides.

JP 10-95771 describes, inter alia, fungicidal benzamidoximes; however, these compounds are, with respect to their fungicidal activity and their biological properties, not entirely satisfactory.

It is an object of the present invention to provide novel benzamidoxime derivatives having improved biological properties and increased activity, in particular also at low application rates.

We have found that this object is achieved by the benzamidoxime derivatives of the formula I

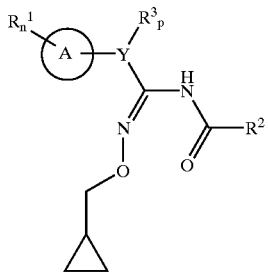

where:

A is an aryl or hetaryl radical from the group consisting of phenyl, pyridyl and thienyl;

Y is a straight-chain or branched $C_1$–$C_4$-alkylene group, where one carbon can be replaced by oxygen, nitrogen or sulfur or by a cyclopropyl group;

$R_n^1$ are one to five identical or different radicals from the group consisting of: hydrogen, halogen, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkoxyalkoxy;

$R^2$ is phenyl-$C_1$–$C_6$-alkyl, which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the phenyl ring, or is thienyl-$C_1$–$C_4$-alkyl, which may carry one or more substituents selected from the group consisting of halogen, $C_1$–$C_4$-alkyl, $C_1$–$C_4$-haloalkyl, $C_1$–$C_4$-alkoxy or $C_1$–$C_4$-haloalkoxy and the thienyl ring, or is pyrazolyl-$C_1$–$C_4$-alkyl, which may carry one or more substituents selected from the group consisting of halogen, $C_1$–$C_4$-alkyl, $C_1$–$C_4$haloalkyl, $C_1$–$C_4$-alkoxy and $C_1$–$C_4$-haloalkoxy on the pyrazole ring, $R_p^3$ are one to five identical or different radicals from the group consisting of: hydrogen, halogen, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkoxyalkoxy, $C_1$–$C_6$-alkylcarbonyl;

n is 0, 1, 2, 3, 4 or 5;

p is, depending on the number of free valencies, 0, 1, 2, 3, 4, and their environmentally compatible and agriculturally utilizable salts.

The integers n and p determine the number of substituents $R^1$ and $R^3$, respectively. If n=0, then $R^1$ is hydrogen. If p=0, then $R^3$ is hydrogen.

In the definition of the radicals given in the formula I, the terms mentioned are collective terms for a group of compounds.

Halogen is in each case fluorine, bromine, chlorine or iodine, in particular fluorine or chlorine.

Other meanings are, for example:

$C_1$–$C_6$-alkyl: methyl, ethyl, n-propyl, 1-methylethyl, n-butyl, 1-methylpropyl, 2-methylpropyl or 1,1-dimethylethyl, in particular $C_1$–$C_4$-alkyl, and also methyl or ethyl;

$C_1$–$C_6$-haloalkyl: a $C_1$–$C_6$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, in particular trifluoromethyl;

$C_1$–$C_4$-alkylene: a straight-chain or branched carbon chain, such as, for example, —$CH_2$—, —$CH_2$—$CH_2$—, —$CH(CH_3)$—, —$CH_2$—$CH(CH_3)$—, $CH(CH_3)$—$CH_2$—, $CH_2$—$CH_2$—$CH_2$—$CH_2$—, —$CH_2$—($CH_3$)—$CH_2$—;

$C_1$–$C_4$-alkylene where one carbon can be replaced by oxygen, sulfur or nitrogen: a $C_1$–$C_4$-alkylene as mentioned above where any carbon can be replaced by a heteroatom X (X=O, S, NH) such as, for example, —X—$CH_2$—, —$CH_2$—X—, —X—$CH_2$—$CH_2$—, —$CH(CH_3)$—X—, —X—$CH_2$—$CH(CH_3)$—, $CH(CH_3)$—$CH_2$—X—, —X—$CH_2$—$CH_2$—$CH_2$—, —$CH_2$—$CH(CH_3)$—$CH_2$—X—;

$C_1$–$C_4$-alkylene where a carbon can be replaced by an unsubstituted or $R_p^3$-substituted cyclopropyl group (cPr): a $C_1$–$C_4$-alkylene as mentioned above where any carbon can be replaced by a heteroatom X (X=O, S, NH), such as, for example, —cPr—, —cPr—$CH_2$—, —$CH_2$—cPr—, —cPr—$CH_2$—$CH_2$—, —$CH(CH_3)$—cPr—, —cPr—$CH_2$—$CH(CH_3)$—, —$CH(CH_3)$—$CH_2$—cPr—, —cPr—$CH_2$—$CH_2$—$CH_2$—, —$CH_2$—$CH(CH_3)$—$CH_2$—cPr;

$C_1$–$C_6$-alkoxy: methoxy, ethoxy, n-propoxy, 1-methylethoxy, n-butoxy, 1-methoxypropoxy, 2-metylpropoxy or 1,1-dimethylethoxy, in particular $C_1$–$C_4$-alkoxy, and also methoxy or ethoxy;

$C_1$–$C_4$-haloalkoxy: a $C_1$–$C_4$-alkoxy radical as mentioned above which is partially or fully substituted by fluorine, chlorine, bromine and/or iodine, i.e. for example chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropyl, 1-(fluoromethyl)-2-fluoroethoxy, 1-(chloromethyl)-2-chloroethoxy, 1-(bromoethyl)-2-bromoethoxy, 4-fluorobutoxy, 4-chlorobutoxy, 4-bromobutyoxy or nonafluorobutoxy, in particular difluoromethoxy;

phenyl-$C_1$–$C_6$-alkyl: for example benzyl, 1-phenylethyl, 2-phenylethyl, 1-phenylprop-1-yl, 2-phenylprop-1-yl, 3-phenylprop-1-yl, 1-(phenylmethyl)eth-1-yl, 1-(phenylmethyl)-1-(methyl)eth-1-yl or 1-(phenylmethyl)prop-1-yl, in particular benzyl or 2-phenylethyl;

thienyl-$C_1$–$C_4$-alkyl: for example 2-thienylmethyl, 3-thienylmethyl, 2-thienylethyl, 2-thienylprop-1-yl or 3-thienylprop-1-yl;

pyrazolyl-$C_1$–$C_4$-alkyl: for example 1-pyrazolylmethyl, 2-pyrazolylmethyl, 3-pyrazolylmethyl, 2-pyrazolylethyl, 2-pyrazolylprop-1-yl or 3-pyrazolylprop-1-yl;

heteroaryl: an aromatic 5- or 6-membered heterocyclic ring which contains one to four identical or different heteroatoms selected from the following group: oxygen, sulfur or nitrogen, and which may be attached to the group Y via a carbon or a heteroatom; for example pyridyl, pyrrolyl, pyrimidinyl, imidazolyl, pyrazolyl, thienyl, oxazinyl, furanyl, oxazolyl, imidoxazolyl;

aryl: an aromatic carboxycyclic, mono- or bicyclic ring having 6–14 carbon atoms, such as, for example, phenyl or naphthyl; in particular phenyl.

Compounds of the formula I in which A is a phenyl group and n is 1, 2 or 3 have generally been found to be particularly effective. $R^1$ is here preferably fluorine, chlorine, methyl, methoxy or trifluoromethyl.

If A is a phenyl group, the substituents $R^1_n$ preferably have the following meanings: 2,6-dichloro; 2-chloro-6-fluoro; 2,6-difluoro; 2-chloro-5,6-dichloro; 2-chloro-6-trifluoromethyl; 2-fluoro-6-trifluoromethyl; 2-bromo-6-trifluoromethyl; 2-iodo-6-trifluoromethyl; 2,6-dibromo; 2-bromo-6-fluoro; 2-bromo-6-chloro; 2-chloro-6-trifluoromethoxy; 2-fluoro-6-trifluoromethoxy; 2-chloro-6-difluoromethoxy; 2-difluoromethoxy-6-fluoro; 2,3-dichloro-6-difluoromethoxy; 2,3-difluoro-6-difluoromethoxy; 2,6-bis(difluoromethoxy); 2,6-bis(trifluoromethoxy); 2,6-bis(trifluoromethyl); 2-bromo; 2-chloro; 2-fluoro; 3-bromo; 3-chloro; 3-fluoro; 4-bromo; 4-chloro; 4-fluoro; 4-methoxy; 2-chloro-6-methylthio; 2,3-difluoro-6-methylthio; 2,4-dichloro; 3,5-dichloro; 2,3,6-trichloro; 2,3,6-trifluoro; 2,3,4,5,6-pentafluoro; 2-fluoro-6-methyl; 2-chloro-6-methyl.

The group $R^2$ is preferably phenylmethyl; (4-chlorophenyl)methyl; (4-fluorophenyl)methyl; (4-methylphenyl)methyl; (3-methylphenyl)methyl; (4-trifluoromethylphenyl)methyl; (4-methoxyphenyl)methyl; (2-thienyl)methyl.

Y is, in particular, a straight-chain or branched $C_1$–$C_3$-alkylene chain, where one carbon can be replaced by oxygen or sulfur or an imino group (—NH—) or alkylamino group (—N(alkyl)—).

Preference is given to compounds of the formula I in which:

A is an aryl or hetaryl radical from the group consisting of phenyl, pyridyl and thienyl;

Y is a carbon;

$R_n^1$ are one to five identical or different radicals from the group consisting of: hydrogen, halogen, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkoxyalkoxy;

$R^2$ is phenyl-$C_1$–$C_6$-alkyl, which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the phenyl ring, or is thienyl-$C_1$–$C_4$-alkyl, which may carry one or more substituents selected from the group consisting of halogen, $C_1$–$C_4$-alkyl, $C_1$–$C_4$-haloalkyl, $C_1$–$C_4$-alkoxy or $C_1$–$C_4$-haloalkoxy on the thienyl ring, or is pyrazolyl-$C_1$–$C_4$-alkyl, which may carry one or more substituents selected from the group consisting of halogen, $C_1$–$C_4$-alkyl, $C_1$–$C_4$haloalkyl, $C_1$–$C_4$-alkoxy and $C_1$–$C_4$-haloalkoxy on the pyrazole ring, $R_p^3$ are hydrogen or $C_1$–$C_4$-alkyl;

n is 0–5;

p is 0–2.

Particular preference is given to compounds of the formula I where:

A is phenyl;

Y is a carbon;

$R_n^1$ are one to five identical or different radicals from the group consisting of: hydrogen, halogen, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkoxyalkoxy;

$R^2$ is phenylmethyl, which may carry one or more substitutents selected from the group consisting of halogen, $C_1$–$C_4$-alkyl, $C_1$–$C_4$-haloalkyl, $C_1$–$C_4$-alkoxy and $C_1$–$C_4$-haloalkoxy on the phenyl ring;

$R_p^3$ is hydrogen or methyl;

n is 0–5;

p is 0–1.

Particular preference is given to compounds of the formula I in which $R^1$ and $R^2$ have the meanings listed in Table 1 below.

TABLE 1

| No. | A | $R^1_n$ | $R^2$ | Y—$R^3_p$ |
|---|---|---|---|---|
| 1) | phenyl | 2,6-dichloro | phenylmethyl | —$CH_2$— |
| 2) | phenyl | 2-chloro-6-fluoro | phenylmethyl | —$CH_2$— |
| 3) | phenyl | 2,6-difluoro | phenylmethyl | —$CH_2$— |
| 4) | phenyl | 2-chloro-5,6-difluoro | phenylmethyl | —$CH_2$— |
| 5) | phenyl |  | phenylmethyl | —$CH_2$— |
| 6) | phenyl | 2-chloro-6-trifluoromethyl | phenylmethyl | —$CH_2$— |
| 7) | phenyl | 2-fluoro-6-trifluoromethyl | phenylmethyl | —$CH_2$— |
| 8) | phenyl | 2-bromo-6-trifluoromethyl | phenylmethyl | —$CH_2$— |
| 9) | phenyl | 2-iodo-6-trifluoromethyl | phenylmethyl | —$CH_2$— |
| 10) | phenyl | 2,6-dibromo | phenylmethyl | —$CH_2$— |
| 11) | phenyl | 2-bromo-6-fluoro | phenylmethyl | —$CH_2$— |

TABLE 1-continued

| No. | A | $R^1_n$ | $R^2$ | $Y-R^3_p$ |
|---|---|---|---|---|
| 12) | phenyl | 2-bromo-6-chloro | phenylmethyl | —CH$_2$— |
| 13) | phenyl | 2-chloro-6-trifluoromethoxy | phenylmethyl | —CH$_2$— |
| 14) | phenyl | 2-fluoro-6-trifluoromethoxy | phenylmethyl | —CH$_2$— |
| 15) | phenyl | 2-chloro-6-difluoromethoxy | phenylmethyl | —CH$_2$— |
| 16) | phenyl | 2-difluoromethoxy-6-fluoro | phenylmethyl | —CH$_2$— |
| 17) | phenyl | 2,3-dichloro-6-difluoro-methoxy | phenylmethyl | —CH$_2$— |
| 18) | phenyl | 2,3-difluoro-6-difluoro-methoxy | phenylmethyl | —CH$_2$— |
| 19) | phenyl | 2,6-bis(difluoromethoxy) | phenylmethyl | —CH$_2$— |
| 20) | phenyl | 2,6-bis(trifluoromethoxy) | phenylmethyl | —CH$_2$— |
| 21) | phenyl | 2,6-bis(trifluoromethyl) | phenylmethyl | —CH$_2$— |
| 22) | phenyl | 2-bromo | phenylmethyl | —CH$_2$— |
| 23) | phenyl | 2-chloro | phenylmethyl | —CH$_2$— |
| 24) | phenyl | 2-fluoro | phenylmethyl | —CH$_2$— |
| 25) | phenyl | 3-bromo | phenylmethyl | —CH$_2$— |
| 26) | phenyl | 3-chloro | phenylmethyl | —CH$_2$— |
| 27) | phenyl | 3-fluoro | phenylmethyl | —CH$_2$— |
| 28) | phenyl | 4-bromo | phenylmethyl | —CH$_2$— |
| 29) | phenyl | 4-chloro | phenylmethyl | —CH$_2$— |
| 30) | phenyl | 4-fluoro | phenylmethyl | —CH$_2$— |
| 31) | phenyl | 4-methoxy | phenylmethyl | —CH$_2$— |
| 32) | phenyl | 2-chloro-6-methylthio | phenylmethyl | —CH$_2$— |
| 33) | phenyl | 2,3-difluoro-6-methylthio | phenylmethyl | —CH$_2$— |
| 34) | phenyl | 2,4-dichloro | phenylmethyl | —CH$_2$— |
| 35) | phenyl | 3,5-dichloro | phenylmethyl | —CH$_2$— |
| 36) | phenyl | 2,3,6-trichloro | phenylmethyl | —CH$_2$— |
| 37) | phenyl | 2,3,6-trifluoro | phenylmethyl | —CH$_2$— |
| 38) | phenyl | 2,3,4,5,6-pentafluoro | phenylmethyl | —CH$_2$— |
| 39) | phenyl | 2-fluoro-6-methyl | phenylmethyl | —CH$_2$— |
| 40) | phenyl | 2-chloro-6-methyl | phenylmethyl | —CH$_2$— |
| 41) | phenyl | 2,6-dichloro | phenylmethyl | —CH$_2$CH$_2$— |
| 42) | phenyl | 2-chloro-6-fluoro | phenylmethyl | —CH$_2$CH$_2$— |
| 43) | phenyl | 2,6-difluoro | phenylmethyl | —CH$_2$CH$_2$— |
| 44) | phenyl | 2-chloro-5,6-difluoro | phenylmethyl | —CH$_2$CH$_2$— |
| 45) | phenyl | 2-chloro-6-trifluoromethyl | phenylmethyl | —CH$_2$CH$_2$— |
| 46) | phenyl | 2-fluoro-6-trifluoromethyl | phenylmethyl | —CH$_2$CH$_2$— |
| 47) | phenyl | 2-bromo-6-trifluoromethyl | phenylmethyl | —CH$_2$CH$_2$— |
| 48) | phenyl | 2-iodo-6-trifluoromethyl | phenylmethyl | —CH$_2$CH$_2$— |
| 49) | phenyl | 2,6-dibromo | phenylmethyl | —CH$_2$CH$_2$— |
| 50) | phenyl | 2-bromo-6-fluoro | phenylmethyl | —CH$_2$CH$_2$— |
| 51) | phenyl | 2-bromo-6-chloro | phenylmethyl | —CH$_2$CH$_2$— |
| 52) | phenyl | 2-chloro-6-trifluoromethoxy | phenylmethyl | —CH$_2$CH$_2$— |
| 53) | phenyl | 2-fluoro-6-trifluoromethoxy | phenylmethyl | —CH$_2$CH$_2$— |
| 54) | phenyl | 2-chloro-6-difluoromethoxy | phenylmethyl | —CH$_2$CH$_2$— |
| 55) | phenyl | 2-difluoromethoxy-6-fluoro | phenylmethyl | —CH$_2$CH$_2$— |
| 56) | phenyl | 2,3-dichloro-6-difluoro-methoxy | phenylmethyl | —CH$_2$CH$_2$— |
| 57) | phenyl | 2,3-difluoro-6-difluoro-methoxy | phenylmethyl | —CH$_2$CH$_2$— |
| 58) | phenyl | 2,6-bis(difluoromethoxy) | phenylmethyl | —CH$_2$CH$_2$— |
| 59) | phenyl | 2,6-bis(trifluoromethoxy) | phenylmethyl | —CH$_2$CH$_2$— |
| 60) | phenyl | 2,6-bis(trifluoromethyl) | phenylmethyl | —CH$_2$CH$_2$— |
| 61) | phenyl | 2-bromo | phenylmethyl | —CH$_2$CH$_2$— |
| 62) | phenyl | 2-chloro | phenylmethyl | —CH$_2$CH$_2$— |
| 63) | phenyl | 2-fluoro | phenylmethyl | —CH$_2$CH$_2$— |
| 64) | phenyl | 3-bromo | phenylmethyl | —CH$_2$CH$_2$— |
| 65) | phenyl | 3-chloro | phenylmethyl | —CH$_2$CH$_2$— |
| 66) | phenyl | 3-fluoro | phenylmethyl | —CH$_2$CH$_2$— |
| 67) | phenyl | 4-bromo | phenylmethyl | —CH$_2$CH$_2$— |
| 68) | phenyl | 4-chloro | phenylmethyl | —CH$_2$CH$_2$— |
| 69) | phenyl | 4-fluoro | phenylmethyl | —CH$_2$CH$_2$— |
| 70) | phenyl | 4-methoxy | phenylmethyl | —CH$_2$CH$_2$— |
| 71) | phenyl | 2-chloro-6-methylthio | phenylmethyl | —CH$_2$CH$_2$— |
| 72) | phenyl | 2,3-difluoro-6-methylthio | phenylmethyl | —CH$_2$CH$_2$— |
| 73) | phenyl | 2,4-dichloro | phenylmethyl | —CH$_2$CH$_2$— |
| 74) | phenyl | 3,5-dichloro | phenylmethyl | —CH$_2$CH$_2$— |
| 75) | phenyl | 2,3,6-trichloro | phenylmethyl | —CH$_2$CH$_2$— |
| 76) | phenyl | 2,3,6-trifluoro | phenylmethyl | —CH$_2$CH$_2$— |
| 77) | phenyl | 2,3,4,5,6-pentafluoro | phenylmethyl | —CH$_2$CH$_2$— |
| 78) | phenyl | 2-fluoro-6-methyl | phenylmethyl | —CH$_2$CH$_2$— |
| 79) | phenyl | 2-chloro-6-methyl | phenylmethyl | —CH$_2$CH$_2$— |
| 80) | phenyl | 2,6-dichloro | (4-chlorophenyl)methyl | —CH$_2$— |
| 81) | phenyl | 2-chloro-6-fluoro | (4-chlorophenyl)methyl | —CH$_2$— |
| 82) | phenyl | 2,6-difluoro | (4-chlorophenyl)methyl | —CH$_2$— |
| 83) | phenyl | 2-chloro-5,6-difluoro | (4-chlorophenyl)methyl | —CH$_2$— |
| 84) | phenyl | 2-chloro-6-trifluoromethyl | (4-chlorophenyl)methyl | —CH$_2$— |

TABLE 1-continued

| No. | A | $R^1_n$ | $R^2$ | $Y-R^3_p$ |
|---|---|---|---|---|
| 85) | phenyl | 2-fluoro-6-trifluoromethyl | (4-chlorophenyl)methyl | —CH$_2$— |
| 86) | phenyl | 2-bromo-6-trifluoromethyl | (4-chlorophenyl)methyl | —CH$_2$— |
| 87) | phenyl | 2-iodo-6-trifluoromethyl | (4-chlorophenyl)methyl | —CH$_2$— |
| 88) | phenyl | 2,6-dibromo | (4-chlorophenyl)methyl | —CH$_2$— |
| 89) | phenyl | 2-bromo-6-fluoro | (4-chlorophenyl)methyl | —CH$_2$— |
| 90) | phenyl | 2-bromo-6-chloro | (4-chlorophenyl)methyl | —CH$_2$— |
| 91) | phenyl | 2-chloro-6-trifluoromethoxy | (4-chlorophenyl)methyl | —CH$_2$— |
| 92) | phenyl | 2-fluoro-6-trifluoromethoxy | (4-chlorophenyl)methyl | —CH$_2$— |
| 93) | phenyl | 2-chloro-6-difluoromethoxy | (4-chlorophenyl)methyl | —CH$_2$— |
| 94) | phenyl | 2-difluoromethoxy-6-fluoro | (4-chlorophenyl)methyl | —CH$_2$— |
| 95) | phenyl | 2,3-dichloro-6-difluoromethoxy | (4-chlorophenyl)methyl | —CH$_2$— |
| 96) | phenyl | 2,3-difluoro-6-difluoromethoxy | (4-chlorophenyl)methyl | —CH$_2$— |
| 97) | phenyl | 2,6-bis(difluoromethoxy) | (4-chlorophenyl)methyl | —CH$_2$— |
| 98) | phenyl | 2,6-bis(trifluoromethoxy) | (4-chlorophenyl)methyl | —CH$_2$— |
| 99) | phenyl | 2,6-bis(trifluoromethyl) | (4-chlorophenyl)methyl | —CH$_2$— |
| 100) | phenyl | 2-bromo | (4-chlorophenyl)methyl | —CH$_2$— |
| 101) | phenyl | 2-chloro | (4-chlorophenyl)methyl | —CH$_2$— |
| 102) | phenyl | 2-fluoro | (4-chlorophenyl)methyl | —CH$_2$— |
| 103) | phenyl | 3-bromo | (4-chlorophenyl)methyl | —CH$_2$— |
| 104) | phenyl | 3-chloro | (4-chlorophenyl)methyl | —CH$_2$— |
| 105) | phenyl | 3-fluoro | (4-chlorophenyl)methyl | —CH$_2$— |
| 106) | phenyl | 4-bromo | (4-chlorophenyl)methyl | —CH$_2$— |
| 107) | phenyl | 4-chloro | (4-chlorophenyl)methyl | —CH$_2$— |
| 108) | phenyl | 4-fluoro | (4-chlorophenyl)methyl | —CH$_2$— |
| 109) | phenyl | 4-methoxy | (4-chlorophenyl)methyl | —CH$_2$— |
| 110) | phenyl | 2-chloro-6-methylthio | (4-chlorophenyl)methyl | —CH$_2$— |
| 111) | phenyl | 2,3-difluoro-6-methylthio | (4-chlorophenyl)methyl | —CH$_2$— |
| 112) | phenyl | 2,4-dichloro | (4-chlorophenyl)methyl | —CH$_2$— |
| 113) | phenyl | 3,5-dichloro | (4-chlorophenyl)methyl | —CH$_2$— |
| 114) | phenyl | 2,3,6-trichloro | (4-chlorophenyl)methyl | —CH$_2$— |
| 115) | phenyl | 2,3,6-trifluoro | (4-chlorophenyl)methyl | —CH$_2$— |
| 116) | phenyl | 2,3,4,5,6-pentafluoro | (4-chlorophenyl)methyl | —CH$_2$— |
| 117) | phenyl | 2-fluoro-6-methyl | (4-chlorophenyl)methyl | —CH$_2$— |
| 118) | phenyl | 2-chloro-6-methyl | (4-chlorophenyl)methyl | —CH$_2$— |
| 119) | phenyl | 2,6-dichloro | (4-fluorophenyl)methyl | —CH$_2$— |
| 120) | phenyl | 2-chloro-6-fluoro | (4-fluorophenyl)methyl | —CH$_2$— |
| 121) | phenyl | 2,6-difluoro | (4-fluorophenyl)methyl | —CH$_2$— |
| 122) | phenyl | 2-chloro-5,6-difluoro | (4-fluorophenyl)methyl | —CH$_2$— |
| 123) | phenyl | 2-chloro-6-trifluoromethyl | (4-fluorophenyl)methyl | —CH$_2$— |
| 124) | phenyl | 2-fluoro-6-trifluoromethyl | (4-fluorophenyl)methyl | —CH$_2$— |
| 125) | phenyl | 2-bromo-6-trifluoromethyl | (4-fluorophenyl)methyl | —CH$_2$— |
| 126) | phenyl | 2-iodo-6-trifluoromethyl | (4-fluorophenyl)methyl | —CH$_2$— |
| 127) | phenyl | 2,6-dibromo | (4-fluorophenyl)methyl | —CH$_2$— |
| 128) | phenyl | 2-bromo-6-fluoro | (4-fluorophenyl)methyl | —CH$_2$— |
| 129) | phenyl | 2-bromo-6-chloro | (4-fluorophenyl)methyl | —CH$_2$— |
| 130) | phenyl | 2-chloro-6-trifluoromethoxy | (4-fluorophenyl)methyl | —CH$_2$— |
| 131) | phenyl | 2-fluoro-6-trifluoromethoxy | (4-fluorophenyl)methyl | —CH$_2$— |
| 132) | phenyl | 2-chloro-6-difluoromethoxy | (4-fluorophenyl)methyl | —CH$_2$— |
| 133) | phenyl | 2-difluoromethoxy-6-fluoro | (4-fluorophenyl)methyl | —CH$_2$— |
| 134) | phenyl | 2,3-dichloro-6-difluoromethoxy | (4-fluorophenyl)methyl | —CH$_2$— |
| 135) | phenyl | 2,3-difluoro-6-difluoromethoxy | (4-fluorophenyl)methyl | —CH$_2$— |
| 136) | phenyl | 2,6-bis(difluoromethoxy) | (4-fluorophenyl)methyl | —CH$_2$— |
| 137) | phenyl | 2,6-bis(trifluoromethoxy) | (4-fluorophenyl)methyl | —CH$_2$— |
| 138) | phenyl | 2,6-bis(trifluoromethyl) | (4-fluorophenyl)methyl | —CH$_2$— |
| 139) | phenyl | 2-bromo | (4-fluorophenyl)methyl | —CH$_2$— |
| 140) | phenyl | 2-chloro | (4-fluorophenyl)methyl | —CH$_2$— |
| 141) | phenyl | 2-fluoro | (4-fluorophenyl)methyl | —CH$_2$— |
| 142) | phenyl | 3-bromo | (4-fluorophenyl)methyl | —CH$_2$— |
| 143) | phenyl | 3-chloro | (4-fluorophenyl)methyl | —CH$_2$— |
| 144) | phenyl | 3-fluoro | (4-fluorophenyl)methyl | —CH$_2$— |
| 145) | phenyl | 4-bromo | (4-fluorophenyl)methyl | —CH$_2$— |
| 146) | phenyl | 4-chloro | (4-fluorophenyl)methyl | —CH$_2$— |
| 147) | phenyl | 4-fluoro | (4-fluorophenyl)methyl | —CH$_2$— |
| 148) | phenyl | 4-methoxy | (4-fluorophenyl)methyl | —CH$_2$— |
| 149) | phenyl | 2-chloro-6-methylthio | (4-fluorophenyl)methyl | —CH$_2$— |
| 150) | phenyl | 2,3-difluoro-6-methylthio | (4-fluorophenyl)methyl | —CH$_2$— |
| 151) | phenyl | 2,4-dichloro | (4-fluorophenyl)methyl | —CH$_2$— |
| 152) | phenyl | 3,5-dichloro | (4-fluorophenyl)methyl | —CH$_2$— |
| 153) | phenyl | 2,3,6-trichloro | (4-fluorophenyl)methyl | —CH$_2$— |
| 154) | phenyl | 2,3,6-trifluoro | (4-fluorophenyl)methyl | —CH$_2$— |
| 155) | phenyl | 2,3,4,5,6-pentafluoro | (4-fluorophenyl)methyl | —CH$_2$— |
| 156) | phenyl | 2-fluoro-6-methyl | (4-fluorophenyl)methyl | —CH$_2$— |
| 157) | phenyl | 2-chloro-6-methyl | (4-fluorophenyl)methyl | —CH$_2$— |

TABLE 1-continued

| No. | A | $R^1_n$ | $R^2$ | $Y-R^3_p$ |
|---|---|---|---|---|
| 158) | phenyl | 2,6-dichloro | (4-methylphenyl)methyl | —$CH_2$— |
| 159) | phenyl | 2-chloro-6-fluoro | (4-methylphenyl)methyl | —$CH_2$— |
| 160) | phenyl | 2,6-difluoro | (4-methylphenyl)methyl | —$CH_2$— |
| 161) | phenyl | 2-chloro-5,6-difluoro | (4-methylphenyl)methyl | —$CH_2$— |
| 162) | phenyl | 2-chloro-6-trifluoromethyl | (4-methylphenyl)methyl | —$CH_2$— |
| 163) | phenyl | 2-fluoro-6-trifluoromethyl | (4-methylphenyl)methyl | —$CH_2$— |
| 164) | phenyl | 2-bromo-6-trifluoromethyl | (4-methylphenyl)methyl | —$CH_2$— |
| 165) | phenyl | 2-iodo-6-trifluoromethyl | (4-methylphenyl)methyl | —$CH_2$— |
| 166) | phenyl | 2,6-dibromo | (4-methylphenyl)methyl | —$CH_2$— |
| 167) | phenyl | 2-bromo-6-fluoro | (4-methylphenyl)methyl | —$CH_2$— |
| 168) | phenyl | 2-bromo-6-chloro | (4-methylphenyl)methyl | —$CH_2$— |
| 169) | phenyl | 2-chloro-6-trifluoromethoxy | (4-methylphenyl)methyl | —$CH_2$— |
| 170) | phenyl | 2-fluoro-6-trifluoromethoxy | (4-methylphenyl)methyl | —$CH_2$— |
| 171) | phenyl | 2-chloro-6-difluoromethoxy | (4-methylphenyl)methyl | —$CH_2$— |
| 172) | phenyl | 2-difluoromethoxy-6-fluoro | (4-methylphenyl)methyl | —$CH_2$— |
| 173) | phenyl | 2,3-dichloro-6-difluoro-methoxy | (4-methylphenyl)methyl | —$CH_2$— |
| 174) | phenyl | 2,3-difluoro-6-difluoro-methoxy | (4-methylphenyl)methyl | —$CH_2$— |
| 175) | phenyl | 2,6-bis(difluoromethoxy) | (4-methylphenyl)methyl | —$CH_2$— |
| 176) | phenyl | 2,6-bis(trifluoromethoxy) | (4-methylphenyl)methyl | —$CH_2$— |
| 177) | phenyl | 2,6-bis(trifluoromethyl) | (4-methylphenyl)methyl | —$CH_2$— |
| 178) | phenyl | 2-bromo | (4-methylphenyl)methyl | —$CH_2$— |
| 179) | phenyl | 2-chloro | (4-methylphenyl)methyl | —$CH_2$— |
| 180) | phenyl | 2-fluoro | (4-methylphenyl)methyl | —$CH_2$— |
| 181) | phenyl | 3-bromo | (4-methylphenyl)methyl | —$CH_2$— |
| 182) | phenyl | 3-chloro | (4-methylphenyl)methyl | —$CH_2$— |
| 183) | phenyl | 3-fluoro | (4-methylphenyl)methyl | —$CH_2$— |
| 184) | phenyl | 4-bromo | (4-methylphenyl)methyl | —$CH_2$— |
| 185) | phenyl | 4-chloro | (4-methylphenyl)methyl | —$CH_2$— |
| 186) | phenyl | 4-fluoro | (4-methylphenyl)methyl | —$CH_2$— |
| 187) | phenyl | 4-methoxy | (4-methylphenyl)methyl | —$CH_2$— |
| 188) | phenyl | 2-chloro-6-methylthio | (4-methylphenyl)methyl | —$CH_2$— |
| 189) | phenyl | 2,3-difluoro-6-methylthio | (4-methylphenyl)methyl | —$CH_2$— |
| 190) | phenyl | 2,4-dichloro | (4-methylphenyl)methyl | —$CH_2$— |
| 191) | phenyl | 3,5-dichloro | (4-methylphenyl)methyl | —$CH_2$— |
| 192) | phenyl | 2,3,6-trichloro | (4-methylphenyl)methyl | —$CH_2$— |
| 193) | phenyl | 2,3,6-trifluoro | (4-methylphenyl)methyl | —$CH_2$— |
| 194) | phenyl | 2,3,4,5,6-pentafluoro | (4-methylphenyl)methyl | —$CH_2$— |
| 195) | phenyl | 2-fluoro-6-methyl | (4-methylphenyl)methyl | —$CH_2$— |
| 196) | phenyl | 2-chloro-6-methyl | (4-methylphenyl)methyl | —$CH_2$— |
| 197) | phenyl | 2,6-dichloro | (3-methylphenyl)methyl | —$CH_2$— |
| 198) | phenyl | 2-chloro-6-fluoro | (3-methylphenyl)methyl | —$CH_2$— |
| 199) | phenyl | 2,6-difluoro | (3-methylphenyl)methyl | —$CH_2$— |
| 200) | phenyl | 2-chloro-5,6-difluoro | (3-methylphenyl)methyl | —$CH_2$— |
| 201) | phenyl | 2-chloro-6-trifluoromethyl | (3-methylphenyl)methyl | —$CH_2$— |
| 202) | phenyl | 2-fluoro-6-trifluoromethyl | (3-methylphenyl)methyl | —$CH_2$— |
| 203) | phenyl | 2-bromo-6-trifluoromethyl | (3-methylphenyl)methyl | —$CH_2$— |
| 204) | phenyl | 2-iodo-6-trifluoromethyl | (3-methylphenyl)methyl | —$CH_2$— |
| 205) | phenyl | 2,6-dibromo | (3-methylphenyl)methyl | —$CH_2$— |
| 206) | phenyl | 2-bromo-6-fluoro | (3-methylphenyl)methyl | —$CH_2$— |
| 207) | phenyl | 2-bromo-6-chloro | (3-methylphenyl)methyl | —$CH_2$— |
| 208) | phenyl | 2-chloro-6-trifluoromethoxy | (3-methylphenyl)methyl | —$CH_2$— |
| 209) | phenyl | 2-fluoro-6-trifluoromethoxy | (3-methylphenyl)methyl | —$CH_2$— |
| 210) | phenyl | 2-chloro-6-difluoromethoxy | (3-methylphenyl)methyl | —$CH_2$— |
| 211) | phenyl | 2-difluoromethoxy-6-fluoro | (3-methylphenyl)methyl | —$CH_2$— |
| 212) | phenyl | 2,3-dichloro-6-difluoro-methoxy | (3-methylphenyl)methyl | —$CH_2$— |
| 213) | phenyl | 2,3-difluoro-6-difluoro-methoxy | (3-methylphenyl)methyl | —$CH_2$— |
| 214) | phenyl | 2,6-bis(difluoromethoxy) | (3-methylphenyl)methyl | —$CH_2$— |
| 215) | phenyl | 2,6-bis(trifluoromethoxy) | (3-methylphenyl)methyl | —$CH_2$— |
| 216) | phenyl | 2,6-bis(trifluoromethyl) | (3-methylphenyl)methyl | —$CH_2$— |
| 217) | phenyl | 2-bromo | (3-methylphenyl)methyl | —$CH_2$— |
| 218) | phenyl | 2-chloro | (3-methylphenyl)methyl | —$CH_2$— |
| 219) | phenyl | 2-fluoro | (3-methylphenyl)methyl | —$CH_2$— |
| 220) | phenyl | 3-bromo | (3-methylphenyl)methyl | —$CH_2$— |
| 221) | phenyl | 3-chloro | (3-methylphenyl)methyl | —$CH_2$— |
| 222) | phenyl | 3-fluoro | (3-methylphenyl)methyl | —$CH_2$— |
| 223) | phenyl | 4-bromo | (3-methylphenyl)methyl | —$CH_2$— |
| 224) | phenyl | 4-chloro | (3-methylphenyl)methyl | —$CH_2$— |
| 225) | phenyl | 4-fluoro | (3-methylphenyl)methyl | —$CH_2$— |
| 226) | phenyl | 4-methoxy | (3-methylphenyl)methyl | —$CH_2$— |
| 227) | phenyl | 2-chloro-6-methylthio | (3-methylphenyl)methyl | —$CH_2$— |
| 228) | phenyl | 2,3-difluoro-6-methylthio | (3-methylphenyl)methyl | —$CH_2$— |
| 229) | phenyl | 2,4-dichloro | (3-methylphenyl)methyl | —$CH_2$— |
| 230) | phenyl | 3,5-dichloro | (3-methylphenyl)methyl | —$CH_2$— |

TABLE 1-continued

| No. | A | R¹ₙ | R² | Y—R³ₚ |
|---|---|---|---|---|
| 231) | phenyl | 2,3,6-trichloro | (3-methylphenyl)methyl | —CH₂— |
| 232) | phenyl | 2,3,6-trifluoro | (3-methylphenyl)methyl | —CH₂— |
| 233) | phenyl | 2,3,4,5,6-pentafluoro | (3-methylphenyl)methyl | —CH₂— |
| 234) | phenyl | 2-fluoro-6-methyl | (3-methylphenyl)methyl | —CH₂— |
| 235) | phenyl | 2-chloro-6-methyl | (3-methylphenyl)methyl | —CH₂— |
| 236) | phenyl | 2,6-dichloro | (4-trifluoromethylphenyl)methyl | —CH₂— |
| 237) | phenyl | 2-chloro-6-fluoro | (4-trifluoromethylphenyl)methyl | —CH₂— |
| 238) | phenyl | 2,6-difluoro | (4-trifluoromethylphenyl)methyl | —CH₂— |
| 239) | phenyl | 2-chloro-5,6-difluoro | (4-trifluoromethylphenyl)methyl | —CH₂— |
| 240) | phenyl | 2-chloro-6-trifluoromethyl | (4-trifluoromethylphenyl)methyl | —CH₂— |
| 241) | phenyl | 2-fluoro-6-trifluoromethyl | (4-trifluoromethylphenyl)methyl | —CH₂— |
| 242) | phenyl | 2-bromo-6-trifluoromethyl | (4-trifluoromethylphenyl)methyl | —CH₂— |
| 243) | phenyl | 2-iodo-6-trifluoromethyl | (4-trifluoromethylphenyl)methyl | —CH₂— |
| 244) | phenyl | 2,6-dibromo | (4-trifluoromethylphenyl)methyl | —CH₂— |
| 245) | phenyl | 2-bromo-6-fluoro | (4-trifluoromethylphenyl)methyl | —CH₂— |
| 246) | phenyl | 2-bromo-6-chloro | (4-trifluoromethylphenyl)methyl | —CH₂— |
| 247) | phenyl | 2-chloro-6-trifluoromethoxy | (4-trifluoromethylphenyl)methyl | —CH₂— |
| 248) | phenyl | 2-fluoro-6-trifluoromethoxy | (4-trifluoromethylphenyl)methyl | —CH₂— |
| 249) | phenyl | 2-chloro-6-difluoromethoxy | (4-trifluoromethylphenyl)methyl | —CH₂— |
| 250) | phenyl | 2-difluoromethoxy-6-fluoro | (4-trifluoromethylphenyl)methyl | —CH₂— |
| 251) | phenyl | 2,3-dichloro-6-difluoromethoxy | (4-trifluoromethylphenyl)methyl | —CH₂— |
| 252) | phenyl | 2,3-difluoro-6-difluoromethoxy | (4-trifluoromethylphenyl)methyl | —CH₂— |
| 253) | phenyl | 2,6-bis(difluoromethoxy) | (4-trifluoromethylphenyl)methyl | —CH₂— |
| 254) | phenyl | 2,6-bis(trifluoromethoxy) | (4-trifluoromethylphenyl)methyl | —CH₂— |
| 255) | phenyl | 2,6-bis(trifluoromethyl) | (4-trifluoromethylphenyl)methyl | —CH₂— |
| 256) | phenyl | 2-bromo | (4-trifluoromethylphenyl)methyl | —CH₂— |
| 257) | phenyl | 2-chloro | (4-trifluoromethylphenyl)methyl | —CH₂— |
| 258) | phenyl | 2-fluoro | (4-trifluoromethylphenyl)methyl | —CH₂— |
| 259) | phenyl | 3-bromo | (4-trifluoromethylphenyl)methyl | —CH₂— |
| 260) | phenyl | 3-chloro | (4-trifluoromethylphenyl)methyl | —CH₂— |
| 261) | phenyl | 3-fluoro | (4-trifluoromethylphenyl)methyl | —CH₂— |
| 262) | phenyl | 4-bromo | (4-trifluoromethylphenyl)methyl | —CH₂— |
| 263) | phenyl | 4-chloro | (4-trifluoromethylphenyl)methyl | —CH₂— |
| 264) | phenyl | 4-fluoro | (4-trifluoromethylphenyl)methyl | —CH₂— |
| 265) | phenyl | 4-methoxy | (4-trifluoromethylphenyl)methyl | —CH₂— |
| 266) | phenyl | 2-chloro-6-methylthio | (4-trifluoromethylphenyl)methyl | —CH₂— |
| 267) | phenyl | 2,3-difluoro-6-methylthio | (4-trifluoromethylphenyl)methyl | —CH₂— |
| 268) | phenyl | 2,4-dichloro | (4-trifluoromethylphenyl)methyl | —CH₂— |
| 269) | phenyl | 3,5-dichloro | (4-trifluoromethylphenyl)methyl | —CH₂— |
| 270) | phenyl | 2,3,6-trichloro | (4-trifluoromethylphenyl)methyl | —CH₂— |
| 271) | phenyl | 2,3,6-trifluoro | (4-trifluoromethylphenyl)methyl | —CH₂— |

TABLE 1-continued

| No. | A | $R^1_n$ | $R^2$ | $Y-R^3_p$ |
|---|---|---|---|---|
| 272) | phenyl | 2,3,4,5,6-pentafluoro | (4-trifluoromethylphenyl)methyl | —CH$_2$— |
| 273) | phenyl | 2-fluoro-6-methyl | (4-trifluoromethylphenyl)methyl | —CH$_2$— |
| 274) | phenyl | 2-chloro-6-methyl | (4-trifluoromethylphenyl)methyl | —CH$_2$— |
| 275) | phenyl | 2,6-dichloro | (4-methoxyphenyl)methyl | —CH$_2$— |
| 276) | phenyl | 2-chloro-6-fluoro | (4-methoxyphenyl)methyl | —CH$_2$— |
| 277) | phenyl | 2,6-difluoro | (4-methoxyphenyl)methyl | —CH$_2$— |
| 278) | phenyl | 2-chloro-5,6-difluoro | (4-methoxyphenyl)methyl | —CH$_2$— |
| 279) | phenyl | 2-chloro-6-trifluoromethyl | (4-methoxyphenyl)methyl | —CH$_2$— |
| 280) | phenyl | 2-fluoro-6-trifluoromethyl | (4-methoxyphenyl)methyl | —CH$_2$— |
| 281) | phenyl | 2-bromo-6-trifluoromethyl | (4-methoxyphenyl)methyl | —CH$_2$— |
| 282) | phenyl | 2-iodo-6-trifluoromethyl | (4-methoxyphenyl)methyl | —CH$_2$— |
| 283) | phenyl | 2,6-dibromo | (4-methoxyphenyl)methyl | —CH$_2$— |
| 284) | phenyl | 2-bromo-6-fluoro | (4-methoxyphenyl)methyl | —CH$_2$— |
| 285) | phenyl | 2-bromo-6-chloro | (4-methoxyphenyl)methyl | —CH$_2$— |
| 286) | phenyl | 2-chloro-6-trifluoromethoxy | (4-methoxyphenyl)methyl | —CH$_2$— |
| 287) | phenyl | 2-fluoro-6-trifluoromethoxy | (4-methoxyphenyl)methyl | —CH$_2$— |
| 288) | phenyl | 2-chloro-6-difluoromethoxy | (4-methoxyphenyl)methyl | —CH$_2$— |
| 289) | phenyl | 2-difluoromethoxy-6-fluoro | (4-methoxyphenyl)methyl | —CH$_2$— |
| 290) | phenyl | 2,3-dichloro-6-difluoromethoxy | (4-methoxyphenyl)methyl | —CH$_2$— |
| 291) | phenyl | 2,3-difluoro-6-difluoromethoxy | (4-methoxyphenyl)methyl | —CH$_2$— |
| 292) | phenyl | 2,6-bis(difluoromethoxy) | (4-methoxyphenyl)methyl | —CH$_2$— |
| 293) | phenyl | 2,6-bis(trifluoromethoxy) | (4-methoxyphenyl)methyl | —CH$_2$— |
| 294) | phenyl | 2,6-bis(trifluoromethyl) | (4-methoxyphenyl)methyl | —CH$_2$— |
| 295) | phenyl | 2-bromo | (4-methoxyphenyl)methyl | —CH$_2$— |
| 296) | phenyl | 2-chloro | (4-methoxyphenyl)methyl | —CH$_2$— |
| 297) | phenyl | 2-fluoro | (4-methoxyphenyl)methyl | —CH$_2$— |
| 298) | phenyl | 3-bromo | (4-methoxyphenyl)methyl | —CH$_2$— |
| 299) | phenyl | 3-chloro | (4-methoxyphenyl)methyl | —CH$_2$— |
| 300) | phenyl | 3-fluoro | (4-methoxyphenyl)methyl | —CH$_2$— |
| 301) | phenyl | 4-bromo | (4-methoxyphenyl)methyl | —CH$_2$— |
| 302) | phenyl | 4-chloro | (4-methoxyphenyl)methyl | —CH$_2$— |
| 303) | phenyl | 4-fluoro | (4-methoxyphenyl)methyl | —CH$_2$— |
| 304) | phenyl | 4-methoxy | (4-methoxyphenyl)methyl | —CH$_2$— |
| 305) | phenyl | 2-chloro-6-methylthio | (4-methoxyphenyl)methyl | —CH$_2$— |
| 306) | phenyl | 2,3-difluoro-6-methylthio | (4-methoxyphenyl)methyl | —CH$_2$— |
| 307) | phenyl | 2,4-dichloro | (4-methoxyphenyl)methyl | —CH$_2$— |
| 308) | phenyl | 3,5-dichloro | (4-methoxyphenyl)methyl | —CH$_2$— |
| 309) | phenyl | 2,3,6-trichloro | (4-methoxyphenyl)methyl | —CH$_2$— |
| 310) | phenyl | 2,3,6-trifluoro | (4-methoxyphenyl)methyl | —CH$_2$— |
| 311) | phenyl | 2,3,4,5,6-pentafluoro | (4-methoxyphenyl)methyl | —CH$_2$— |
| 312) | phenyl | 2-fluoro-6-methyl | (4-methoxyphenyl)methyl | —CH$_2$— |
| 313) | phenyl | 2-chloro-6-methyl | (4-methoxyphenyl)methyl | —CH$_2$— |
| 314) | phenyl | 2,6-dichloro | (2-thienyl)methyl | —CH$_2$— |
| 315) | phenyl | 2-chloro-6-fluoro | (2-thienyl)methyl | —CH$_2$— |
| 316) | phenyl | 2,6-difluoro | (2-thienyl)methyl | —CH$_2$— |
| 317) | phenyl | 2-chloro-5,6-difluoro | (2-thienyl)methyl | —CH$_2$— |
| 318) | phenyl | 2-chloro-6-trifluoromethyl | (2-thienyl)methyl | —CH$_2$— |
| 319) | phenyl | 2-fluoro-6-trifluoromethyl | (2-thienyl)methyl | —CH$_2$— |
| 320) | phenyl | 2-bromo-6-trifluoromethyl | (2-thienyl)methyl | —CH$_2$— |
| 321) | phenyl | 2-iodo-6-trifluoromethyl | (2-thienyl)methyl | —CH$_2$— |
| 322) | phenyl | 2,6-dibromo | (2-thienyl)methyl | —CH$_2$— |
| 323) | phenyl | 2-bromo-6-fluoro | (2-thienyl)methyl | —CH$_2$— |
| 324) | phenyl | 2-bromo-6-chloro | (2-thienyl)methyl | —CH$_2$— |
| 325) | phenyl | 2-chloro-6-trifluoromethoxy | (2-thienyl)methyl | —CH$_2$— |
| 326) | phenyl | 2-fluoro-6-trifluoromethoxy | (2-thienyl)methyl | —CH$_2$— |
| 327) | phenyl | 2-chloro-6-difluoromethoxy | (2-thienyl)methyl | —CH$_2$— |
| 328) | phenyl | 2-difluoromethoxy-6-fluoro | (2-thienyl)methyl | —CH$_2$— |
| 329) | phenyl | 2,3-dichloro-6-difluoromethoxy | (2-thienyl)methyl | —CH$_2$— |
| 330) | phenyl | 2,3-difluoro-6-difluoromethoxy | (2-thienyl)methyl | —CH$_2$— |
| 331) | phenyl | 2,6-bis(difluoromethoxy) | (2-thienyl)methyl | —CH$_2$— |
| 332) | phenyl | 2,6-bis(trifluoromethoxy) | (2-thienyl)methyl | —CH$_2$— |
| 333) | phenyl | 2,6-bis(trifluoromethyl) | (2-thienyl)methyl | —CH$_2$— |
| 334) | phenyl | 2-bromo | (2-thienyl)methyl | —CH$_2$— |
| 335) | phenyl | 2-chloro | (2-thienyl)methyl | —CH$_2$— |
| 336) | phenyl | 2-fluoro | (2-thienyl)methyl | —CH$_2$— |
| 337) | phenyl | 3-bromo | (2-thienyl)methyl | —CH$_2$— |
| 338) | phenyl | 3-chloro | (2-thienyl)methyl | —CH$_2$— |
| 339) | phenyl | 3-fluoro | (2-thienyl)methyl | —CH$_2$— |
| 340) | phenyl | 4-bromo | (2-thienyl)methyl | —CH$_2$— |
| 341) | phenyl | 4-chloro | (2-thienyl)methyl | —CH$_2$— |

TABLE 1-continued

| No. A | $R^1_n$ | $R^2$ | $Y-R^3_p$ |
|---|---|---|---|
| 342) phenyl | 4-fluoro | (2-thienyl)methyl | —CH$_2$— |
| 343) phenyl | 4-methoxy | (2-thienyl)methyl | —CH$_2$— |
| 344) phenyl | 2-chloro-6-methylthio | (2-thienyl)methyl | —CH$_2$— |
| 345) phenyl | 2,3-difluoro-6-methylthio | (2-thienyl)methyl | —CH$_2$— |
| 346) phenyl | 2,4-dichloro | (2-thienyl)methyl | —CH$_2$— |
| 347) phenyl | 3,5-dichloro | (2-thienyl)methyl | —CH$_2$— |
| 348) phenyl | 2,3,6-trichloro | (2-thienyl)methyl | —CH$_2$— |
| 349) phenyl | 2,3,6-trifluoro | (2-thienyl)methyl | —CH$_2$— |
| 350) phenyl | 2,3,4,5,6-pentafluoro | (2-thienyl)methyl | —CH$_2$— |
| 351) phenyl | 2-fluoro-6-methyl | (2-thienyl)methyl | —CH$_2$— |
| 352) phenyl | 2-chloro-6-methyl | (2-thienyl)methyl | —CH$_2$— |
| 353) phenyl | 2,6-dichloro | phenylmethyl | —CH(CH$_3$)— |
| 354) phenyl | 2-chloro-6-fluoro | phenylmethyl | —CH(CH$_3$)— |
| 355) phenyl | 2,6-difluoro | phenylmethyl | —CH(CH$_3$)— |
| 356) phenyl | 2-chloro-5,6-difluoro | phenylmethyl | —CH(CH$_3$)— |
| 357) phenyl | 2-chloro-6-trifluoromethyl | phenylmethyl | —CH(CH$_3$)— |
| 358) phenyl | 2-fluoro-6-trifluoromethyl | phenylmethyl | —CH(CH$_3$)— |
| 359) phenyl | | phenylmethyl | —CH(CH$_3$)— |
| 360) phenyl | 2,6-dichloro | phenylmethyl | —O—CH$_2$— |
| 361) phenyl | 2-chloro-6-fluoro | phenylmethyl | —O—CH$_2$— |
| 362) phenyl | 2,6-difluoro | phenylmethyl | —O—CH$_2$— |
| 363) phenyl | 2-chloro-5,6-difluoro | phenylmethyl | —O—CH$_2$— |
| 364) phenyl | 2-chloro-6-trifluoromethyl | phenylmethyl | —O—CH$_2$— |
| 365) phenyl | 2-fluoro-6-trifluoromethyl | phenylmethyl | —O—CH$_2$— |
| 366) phenyl | | phenylmethyl | —O—CH$_2$— |
| 367) 2-pyridyl | | phenylmethyl | —CH$_2$— |
| 368) 3-pyridyl | | phenylmethyl | —CH$_2$— |
| 369) 2-pyridyl | 3-chloro | phenylmethyl | —CH$_2$— |
| 370) 2-thienyl | 3-chloro | phenylmethyl | —CH$_2$— |
| 371) 3-pyridyl | 4-chloro | phenylmethyl | —CH$_2$— |
| 372) 3-pyridyl | 4-trifluoromethyl | phenylmethyl | —CH$_2$— |
| 373) 3-pyridyl | 2-methyl-4-trifluoromethyl | phenylmethyl | —CH$_2$— |
| 374) phenyl | 2,3-dichloro | phenylmethyl | —CH$_2$— |

The amidoximes of the formula III are obtained by reaction of nitriles of the formula II with hydroxylamine or salts thereof in aqueous solution, preferably in water or water/alkanol mixtures, if appropriate in the presence of a base. The amidoximes can then be alkylated in a manner known per se to give the precursors IV, preferred alkylating agents being cyclopropylmethyl bromide or cyclopropylmethyl chloride. The iodide and organic sulfonic acid radicals are likewise suitable for activating the cyclopropylmethyl radical.

The compounds of the formula I can preferably be prepared according to the following scheme:

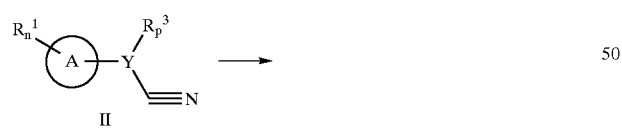

II

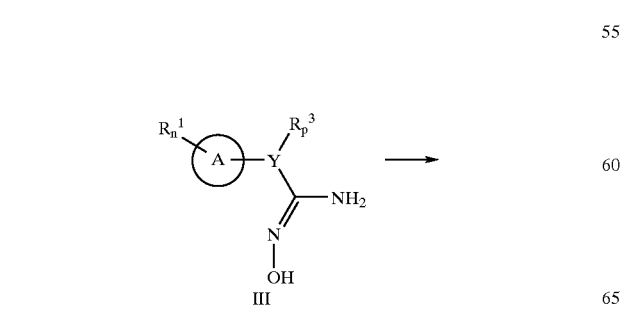

III

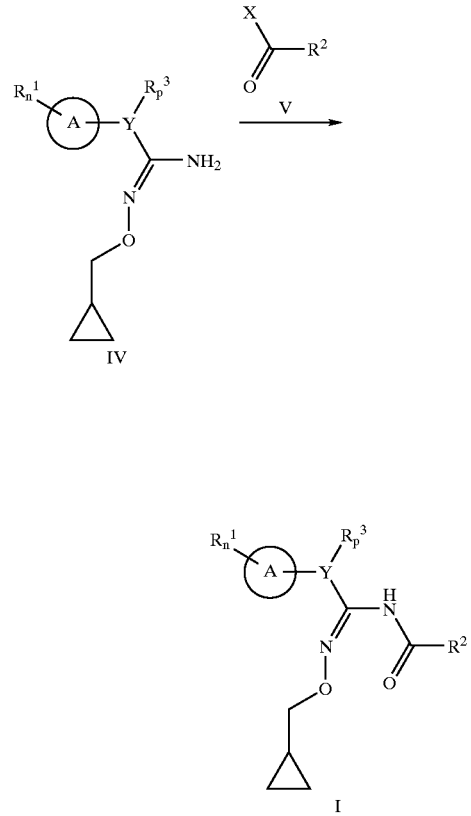

The amidoximes IV can then be acylated in a manner known per se with the corresponding acid derivatives V, preferably with the corresponding acid chlorides or acid anhydrides, by heating in inert solvents (preferably at temperatures in the range from 20 to 100° C.). Suitable inert solvents are, in particular, hydrocarbons or ethers, particularly preferably aromatic hydrocarbons, such as toluene and xylene, to name but two examples.

The intermediates of the formula III and the intermediates of the formula IV mentioned in the reaction scheme above are novel and also form part of the subject matter of the present invention. Preferred amidoixmes of the formula III are the compounds mentioned in Table 2:

TABLE 2

| A | $R^1_n$ | $Y-R^3_p$ | Physical data |
|---|---|---|---|
| phenyl | 2,6-dichloro | —$CH_2$— | m.p. 172–173° C. |
| phenyl | 2-chloro-6-fluoro | —$CH_2$— | m.p. 138–141° C. |
| phenyl | 2,3,6-trifluoro | —$CH_2$— | m.p. 151–153° C. |
| phenyl | | —$CH_2$— | m.p. 39–42° C. |
| phenyl | | —$CH(CH_3)$— | m.p. 85–88° C. |
| phenyl | 2,6-difluoro | —$CH_2$— | m.p. 124–126° C. |
| phenyl | 3,5-dichloro | —$CH_2$— | m.p. 103–107° C. |
| phenyl | 2,3-dichloro | —$CH_2$— | m.p. 162–163° C. |
| phenyl | 2,3,6-trichloro | —$CH_2$— | $^1$H-NMR (CDCl$_3$) δ = 3.90 (s); 4.63(s); 7.25–7.40 (m); 7.43(broadened). |
| phenyl | 2-fluoro-6-trifluoromethyl | —$CH_2$— | $^1$H-NMR (CDCl$_3$) δ = 3.72 (s); 4.58(s); 7.20–7.50(m). |
| phenyl | 2-chloro | —$CH_2$— | $^1$H-NMR (CDCl$_3$) δ = 3.63 (s); 4.63(s); 7.22(m); 7.35(m); 8.67 (broadened). |
| phenyl | 2,4-dichloro | —$CH_2$— | m.p. 155–157° C. |

Preferred amidoxime derivatives of the formula I are the compounds mentioned in Table 3, wherein $R^2$ is benzyl:

TABLE 3

I

| A | $R^1_n$ | $Y-R^3_p$ | Physical data |
|---|---|---|---|
| phenyl | 2,3-difluoro-6-difluoromethoxy | —$CH_2$— | $^1$H-NMR (CDCl$_3$) δ = 0.02 (s); 0.43(m); 0.85(m), 3.55(d); 3.70(s); 4.20(s); 6.35(t); 6.87(m); 7.05(m); 7.25–7.45(m); 8.40(s) |
| phenyl | 2-trifluoromethyl | —$CH_2$— | m.p. 66–67° C. |
| phenyl | 2-fluoro-5-trifluoromethyl | —$CH_2$— | m.p. 65–67° C. |
| phenyl | 2-trifluoromethoxy | —$CH_2$— | m.p. 59–62° C. |
| phenyl | 2-chloro-3,6-difluoro | —$CH_2$— | m.p. 87–88° C. |
| phenyl | 2,3,5-trifluoro | —$CH_2$— | m.p. 74–75° C. |
| phenyl | 2-chlor-5-trifluoromethyl | —$CH_2$— | m.p. 64° C. |
| phenyl | 6-chloro-2-fluoro-3-methyl | —$CH_2$— | m.p. 101° C. |
| phenyl | 2-chloro-6-fluoro-3-methyl | —$CH_2$— | m.p. 96° C. |
| phenyl | 2,3-difluoro-6-methoxy | —$CH_2$— | m.p. 63–65° C. |
| phenyl | 2,6-difluoro-3-methyl | —$CH_2$— | m.p. 72° C. |
| phenyl | 2,6-dimethyl | —$CH_2$— | m.p. 80–81° C. |
| phenyl | 3,5-dichloro | —$CH_2$— | m.p. 53–57° C. |
| phenyl | 2-chloro-6-fluoro | —$CH_2$— | m.p. 42–43° C. |
| phenyl | 2,6-dichloro | —$CH_2$— | m.p. 65–67° C. |
| phenyl | 2,3-dichloro | —$CH_2$— | m.p. 46–48° C. |
| phenyl | 2,3,6-trichloro | —$CH_2$— | m.p. 78–81° C. |
| phenyl | 2-fluoro-6-trifluoromethyl | —$CH_2$— | m.p. 49–51° C. |
| phenyl | H | —$CH_2$— | $^1$H-NMR (CDCl$_3$) δ = 0.28 (m); 0.54(m); 1.15(m); 3.46(s); 3.80(d); 4.45(s); 7.23–7.53(m). |
| phenyl | H | —$CH(CH_3)$— | $^1$H-NMR (CDCl$_3$) δ = 0.30 (m); 0.53(m); 1.15(m); 1.50(d); 3.63(q); 3.83(d); 4.33(s); 7.23–7.37(m). |
| phenyl | 2,6-difluoro | —$CH_2$— | $^1$H-NMR (CDCl$_3$) δ = 0.25 (m); 0.50(m); 1.10(m); 3.53(s); 3.78(d); 4.60(s); 6.90(m); 7.23(m). |
| phenyl | 2,3,6-trifluoro | —$CH_2$— | $^1$H-NMR (CDCl$_3$) δ = 0.25 (m); 0.50(m); 1.10(m); 3.53(s); 3.76(d); 4.60(s); 6.87(m); 7.07(m). |
| phenyl | 2-chloro | —$CH_2$— | $^1$H-NMR (CDCl$_3$) δ = 0.26 (m); 0.52(m); 1.13(m); 3.62(s); 3.80(d); 4.60(s); 7.22(m); 7.40(m). |
| phenyl | 2,4-dichloro | —$CH_2$— | $^1$H-NMR (CDCl$_3$) δ = 0.27 (m); 0.55(m); 1.13(m); 3.57(s); 3.80(d); 4.58(s); 7.18–7.43(m). |

The compounds I have an outstanding activity against a broad range of phytopathogenic fungi, in particular from the classes of the Ascomycetes, Deuteromycetes, Phycomycetes and Basidiomycetes. Some of them act systemically and can therefore also be employed as foliar- and soil-acting fungicides.

The plants are usually sprayed or dusted with the active compounds, or the seeds of the plants are treated with the active compounds.

The formulations are prepared in a known manner, for example by extending the active compound with solvents and/or carriers, if desired using emulsifiers and dispersants, where, if the diluent used is water, it is also possible to use other organic solvents as auxiliary solvents. Suitable auxiliaries are essentially: solvents, such as aromatic compounds (for example xylene), chlorinated aromatic compounds (for example chlorobenzenes), paraffins (for example mineral oil fractions), alcohols (for example methanol, butanol), ketones (for example cyclohexanone), amines (for example ethanolamine, dimethylformamide) and water; carriers such as ground natural minerals (for example kaolins, clays, talc, chalk) and ground synthetic minerals (for example finely divided silica, silicates); emulsifiers, such as nonionic and anionic emulsifiers (for example polyoxyethylene fatty alcohol ethers, alkylsulfonates and arylsulfonates), and dispersants, such as ligninsulfite waste liquors and methyl cellulose.

Suitable surfactants are the alkali metal salts, alkaline earth metal salts and ammonium salts of aromatic sulfonic acids, for example ligno-, phenol-, naphthalene- and dibutylnaphthalenesulfonic acid, and of fatty acids, alkylsulfonates and alkylarylsulfonates, alkyl sulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenyl, alkylphenyl or tributylphenyl polyglycol ether, alkylaryl polyether alcohols, isotridecyl alochol, fatty alcohol ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for scattering and dusts can be prepared by mixing or jointly grinding the active compounds with a solid carrier.

Granules, for example coated granules, impregnated granules or homogeneous granules, can be prepared by binding the active compounds to solid carriers. Solid carriers are mineral earths such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas and products of vegetable origin, such as cereal meal, tree bark meal, wood meal and nutshell meal, cellulose powders or other solid carriers.

Examples of such preparations are:

I. a solution of 90 parts by weight of a compound I according to the invention and 10 parts by weight of N-methyl-2-pyrrolidone, which is suitable for use in the form of microdrops;

II. a mixture of 10 parts by weight of a compound I according to the invention, 70 parts by weight of xylene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of the adduct of 40 mol of ethylene oxide to 1 mol of castor oil; a dispersion is obtained by finely distributing the solution in water;

III. an aqueous dispersion of 10 parts by weight of a compound I according to the invention, 40 parts by weight of cyclohexanone, 30 parts by weight of isobutanol, 20 parts by weight of the adduct of 40 mol of ethylene oxide to 1 mol of castor oil;

IV. an aqueous dispersion of 10 parts by weight of a compound I according to the invention, 25 parts by weight of cyclohexanol, 55 parts by weight of a mineral oil fraction of boiling point 210 to 280° C. and 10 parts by weight of the adduct of 40 mol of ethylene oxide to 1 mol of castor oil;

V. a mixture, ground in a hammer mill, of 80 parts by weight of a compound I according to the invention, preferably in solid form, 3 parts by weight of sodium diisobutylnaphthalene-2-sulfonate, 10 parts by weight of the sodium salt of a lignosulfonic acid from a sulfite waste liquor and 7 parts by weight of pulverulent silica gel; a spray mixture is obtained by finely distributing the mixture in water;

VI. an intimate mixture of 3 parts by weight of a compound I according to the invention and 97 parts by weight of finely divided kaolin; this dust comprises 3% by weight of active compound;

VII. an intimate mixture of 30 parts by weight of a compound I according to the invention, 62 parts by weight of pulverulent silica gel and 8 parts by weight of paraffin oil which has been sprayed onto the surface of this silica gel; this formulation imparts good adhesion to the active compounds;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water, it being possible for this dispersion to be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 50 parts by weight of a paraffinic mineral oil.

The novel compounds have an outstanding activity against a broad range of phytopathogenic fungi, in particular from the classes of the Deuteromycetes, Ascomycetes, Phycomycetes and Basidiomycetes. Some of them act systemically and can be employed as foliar- and soil-acting fungicides.

They are especially important for controlling a large number of fungi in a variety of crops, such as wheat, rye, barley, oats, rice, maize, lawns, cotton, soy, coffee, sugar cane, grapevines, fruit species, ornamentals and vegetable species such as cucumbers, beans and cucurbits as well as in the seeds of these plants.

The compounds are applied by treating the fungi or the seeds, plants, materials or the soil to be kept free from them with a fungicidally effective amount of the active compounds.

Application is effected before or after infection of the materials, plants or seeds by the fungi.

Specially, the novel compounds are suitable for controlling the following plant diseases:

Erysiphe graminis (powdery mildew) in cereals, Erysiphe cichoracearum and Sphaerotheca fuliginea in cucurbits, Podosphaera leucotricha in apples, Uncinula necator in grapevines, Puccinia species in cereals, Rhizoctonia species in cotton and lawns, Ustilago species in cereals and sugar cane, Venturia inaequalis (scab) in apples, Helminthosporium species in cereals, Septoria nodorum in wheat, Botrytis cinerea (gray mold) in strawberries, grapevines, ornamentals and vegetables, Cercospora arachidicola in groundnuts, Pseudocercosporella herpotrichoides in wheat and barley, Pyricularia oryzae in rice, Phytophthora infestanspin potatoes and tomatoes, Fusarium and Verticillium species in a variety of plants, Plasmopara viticola in grapevines, Alternaria species in vegetable and fruit.

The novel compounds can also be used in the protection of materials (wood protection), for example against Paecilomyces variotii.

In general, the fungicidal compositions comprise from 0.1 to 95, preferably from 0.5 to 90, % by weight of active compound.

Depending on the nature of the desired effect, the rates of application are from 0.025 to 2, preferably from 0.1 to 1, kg of active compound per ha.

In the treatment of seed, amounts of from 0.001 to 50 g, preferably 0.01 to 10 g, of active compound are generally required per kilogram of seed.

The compositions according to the invention in the use form as fungicides may also be present together with other active compounds, e.g. with herbicides, insecticides, growth regulators, fungicides or else with fertilizers.

In many cases, a mixture with fungicides results in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron dimethyldithiocarbamate, zinc dimethyldithiocarbamate, zinc ethylenebisdithiocarbamate, manganese ethylenebisdithiocarbamate, manganese zinc ethylenediamine-bis-dithiocarbamate, tetramethylthiuram disulfide, ammonia complex of zinc (N,N-ethylene-bis-dithiocarbamate), ammonia complex of zinc (N,N'-propylene-bis-dithiocarbamate), zinc (N,N'-propylenebisdithiocarbamate), N,N'-polypropylenebis (thiocarbamoyl) disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis (dimethylamino)phosphinyl]-3-phenyl-1,2,4-triazole, 2,3-dicyano-1,4-dithioanthraquinone, 2-thio-1,3-dithiolo [4,5-b]quinoxaline, methyl 1-(butylcarbamoyl)-2-benzimidazolecarbamate, 2-methoxycarbonylaminobenzimidazole, 2-(furyl-(2)) benzimidazole, 2-(thiazolyl-(4))benzimidazole, N-(1,1,2, 2-tetrachloroethylthio)tetrahydrophthalimide, N-trichloromethylthiotetrahydrophthalimide, N-trichloromethylthiophthalamide, N-dichlorofluoromethylthio-N',N'-dimethyl-N-phenylsulfuric diamide, 5-ethoxy-3-trichloromethyl-1,2, 3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thione 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxanthiine, 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecylmorpholino or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2, 4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, (2-chlorophenyl)-(4-chlorophenyl)-5-pyrimidine-methanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, [2-(4-chlorophenyl)ethyl]-1-(1,1-dimethylethyl)-1H-1,2,4-triazole-1-ethanol, 1-[3-(2-chlorophenyl)-1-(4-fluorophenyl)oxiran-2-ylmethyl]-1H-1,2,4-triazole, and a variety of fungicides, such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-iso-propylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-a-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole, strobilurins, such as methyl E-methoximino-[a-(o-tolyloxy)-o-(tolyl]acetate, methyl E-2-{2-[6-(2-cyanophenoxy) pyridimin-4-yloxy]phenyl}-3-methoxyacrylate, N-methyl-E-methoximino-[a-(2,5-dimethylphenoxy)-o-tolyl]acetamide.

anilinopyrimidines, such as N-(4,6-dimethylpyrimidin-2-yl) aniline, N-[4-methyl-6-(1-propynyl)pyrimidin-2-yl] aniline, N-(4-methyl-6-cyclopropylpyrimidin-2-yl) aniline.

phenylpyrroles, such as 4-(2,2-difluoro-1,3-benzodioxol-4-yl]pyrrole-3-carbonitrile.

cinnamamides, such as 3-(4-chlorophenyl)-3-(3,4-dimethoxyphenyl)acryloylmorpholide.

EXAMPLE 1

O-cyclopropylmethyl N-phenylacetyl-(2,6-dichlorophenyl)acetamidoxime (Compound No. 1 from Table 1)

a) (2,6-dichlorophenyl)acetamidoxime 15.0 g (81 mmol) of (2,6-dichlorophenyl)acetonitrile in 60 ml of ethanol were admixed with 10.3 g (148 mmol) of hydroxylamine hydrochloride and then with 11.1 g (105 mmol) of sodium carbonate dissolved in 40 ml of water. This mixture was refluxed for 4 h, poured into aqueous sodium dihydrogen phosphate buffer (pH 7–8) and extracted with methylene chloride. The resulting white solid precipitate (14.0 g) was filtered off and dried under reduced pressure. More product (3.1 g) was obtained from the extract after removal of the solvent under reduced pressure. The overall yield was 17.1 g, m.p. 172–173° C.

b) O-cyclopropylmethyl (2,6-dichlorophenyl) acetamidoxime 10.0 g (46 mmol) of (2,6-dichlorophenyl)acetamidoxime in 40 ml of dimethylformamide were admixed with 6.5 g (48 mmol) of cyclopropylmethyl bromide. The mixture was cooled to −20° C. and admixed dropwise with 5.4 g (48 mmol) of potassium tert-butoxide in 20 ml of dimethylformamide. The mixture was stirred at −20° C. for 1 h and then at room temperature overnight, poured into aqueous sodium dihydrogen phosphate buffer (pH 6) and extracted 5 times with diethyl ether. The combined extracts were washed twice with water and once with saturated sodium chloride solution, dried over sodium sulfate and concentrated under reduced pressure. Yield: 12.3 g of a yellow oil which was reacted further without any further purification.

c) O-cyclopropylmethyl N-phenylacetyl-(2,6-dichlorophenyl)acetamidoxime 5.0 g (18 mmol) of O-cyclopropylmethyl (2,6-dichlorophenyl)acetamidoxime in 40 ml of toluene were heated to 85° C. and admixed with 3.9 (25 mmol) of phenylacetyl chloride. The mixture was heated at 100° C. for 5 h, cooled, poured into aqueous sodium hydrogen carbonate solution (pH 7) and extracted three times with toluene. The combined extracts were washed with water, dried over sodium sulfate and concentrated under reduced pressure. The crude product (5.6 g) was purified by silica gel chromatography using cyclohexane/ethyl acetate. M.p. 134–135° C.

EXAMPLE 2

O-cyclopropylmethyl N-phenylacetyl-(2-chloro-6-fluorophenyl)acetamidoxime (Compound No. 2 from Table 1)

a) (2-chloro-6-fluorophenyl)acetamidoxime 10.0 g (59 mmol) of (2-chloro-6-fluorophenyl)acetonitrile in 50 ml of ethanol were admixed with 7.0 g (101 mmol) of hydroxylamine hydrochloride and then with 7.5 g (71 mmol) of sodium carbonate dissolved in 30 ml of water. This mixture was refluxed for 4 h, poured into aqueous sodium dihydrogen phosphate buffer (pH 7.8) and extracted with methylene chloride, and the extract was dried over sodium sulfate. The solvent was removed under reduced pressure, and 4.9 g of product were obtained from the extract. A further 3.7 g precipitated from the aqueous phase. Overall yield: 8.6 g, which were directly reacted further.

b) O-cyclopropylmethyl (2-chloro-6-fluorophenyl) acetamidoxime 4.0 g (20 mmol) of (2-chloro-6-fluorophenyl) acetamidoxime in 30 ml of dimethylformamide were admixed with 2.8 g (21 mmol) of cyclopropylmethylbromide. The mixture was cooled to −20° C. and admixed dropwise with 2.4 g (21 mmol) of potassium tert-butoxide in 20 ml of dimethylformamide. This mixture was stirred at −20° C. for 1 h and then at room temperature overnight, poured into aqueous sodium dihydrogen phosphate buffer (pH 6) and extracted 5 times with ethyl diethyl ether. The combined extracts were washed twice with water and once with saturated sodium chloride solution, dried over sodium sulfate and concentrated under reduced pressure. Yield 4.8 g of a yellow oil which was reacted further without any further purification.

c) O-cyclopropylmethyl N-phenylacetyl-(2-chloro-6-fluorophenyl)acetamidoxime 3.0 g (12.0 mmol) of O-cyclopropylmethyl (2-chloro-6-fluorophenyl)acetamidoxime in 30 ml of toluene were heated to 85° C. and admixed with 2.5 g (16 mmol) of phenylacetylchloride. The mixture was heated at 100° C. for 5 h, cooled, poured into aqueous sodium hydrogen carbonate solution (pH 7) and extracted three times with toluene. The combined extracts were washed with water, dried over sodium sulfate and concentrated under reduced pressure. The crude product (3.8 g) was purified by silica gel chromatography using cyclohexane/ethyl acetate. Yield 1.5 g of m.p. 109–110° C.

EXAMPLE 3

The following compounds were prepared by the methods described in Examples 1 and 2:

| Compound from Table 1 | Physical data |
|---|---|
| No. 3 | m.p. 75–78° C. |
| No. 5 | $^1$H-NMR (CDCl$_3$) δ = 0.17(m); 0.48(m); 0.97(m); 3.56 (s); 3.75(d); 4.03(s); 7.10–7.25(m); 8.23(s). |
| No. 7 | $^1$H-NMR (CDCl$_3$) δ = −0.05(m); 0.35(m); 0.79(m); 3.50 (d); 3.73(s); 4.32(s); 7.10–7.45(m); 8.43(s). |
| No. 23 | m.p. 69–72° C. |
| No. 34 | m.p. 94–96° C. |
| No. 35 | m.p. 76–80° C. |
| No. 36 | m.p. 95–98° C. |
| No. 37 | m.p. 58–61° C. |
| No. 359 | $^1$H-NMR (CDCl$_3$) δ = 0.20(m); 0.48(m); 1.00(m): 1.38 (d); 3.50(m); 3.78(d); 4.87(q); 7.05–7.35(m); 8.19(s). |
| No. 374 | m.p. 63–65° C. |

EXAMPLE 4

Activity Against Mildew of Wheat

Leaves of wheat seedlings c.v. "Kanzler" which had been grown in pots were sprayed to run off point with an aqueous preparation of active compound which had been prepared from a stock solution comprising 10% of active compound, 63% of cyclohexanone and 27% of emulsifier, and 24 hours after the spray coating had dried on, dusted with spores of powdery mildew of wheat (Erysiphe graminis form a specialis tritici). The test plants were then placed in a greenhouse at 20–24° C. and 60–90% relative atmospheric humidity. After 7 days, the extent of the mildew development was determined visually in percent infection of the total leaf area.

| Active compound No. from Table 1 | % infection of the leaves after application of an aqueous preparation comprising 16 ppm of active compound |
|---|---|
| No. 1 | 3 |
| No. 2 | 3 |
| Untreated | 95 |

The plants which had been treated with the active compounds Nos. 1 and 2 of Table 1 showed an infection of only 3%, whereas the untreated plants were infected to 95%.

EXAMPLE 5

Protective Activity Against Cucumber Mildew

At the two-leaf stage, leaves of cucumber seedlings c.v. "Chinesische Schlange" which had been grown in pots were sprayed to run off point with an aqueous preparation of active compound which had been prepared from a stock solution comprising 10% of active compound, 63% of cyclohexanone and 27% emulsifier. 20 hours after the spray coating had dried on, the plants were inoculated with an aqueous spore suspension of cucumber mildew (*Sphaerotheca fuliginea*). The plants were then cultivated in a greenhouse at 20–24° C. and 60–80% relative atmospheric humidity for 20 days. The extent of the mildew development was then determined visually in % infection of the total leaf area.

| Active compound No. from Table 1 | % infection of the leaves after application of an aqueous preparation comprising 63 ppm of active compound |
|---|---|
| Active compound No. 1 | 10 |
| Active compound No. 2 | 10 |
| Untreated | 90 |

We claim:

1. A benzamidoxime derivative of the formula I

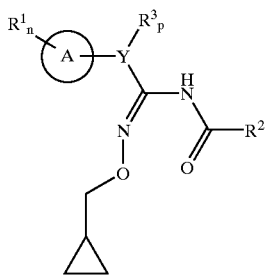

I where:
A is an aryl or hetaryl radical from the group consisting of phenyl, pyridyl and thienyl;
Y is a straight-chain or branched $C_1$–$C_4$-alkylene group, where one carbon can be replaced by oxygen, nitrogen or sulfur or by a cyclopropyl group;
$R_n^1$ are one to five identical or different radicals from the group consisting of: hydrogen, halogen, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkoxyalkoxy;
$R^2$ is phenyl-$C_1$–$C_6$-alkyl, which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the phenyl ring, or
is thienyl-$C_1$–$C_4$-alkyl, which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the thienyl ring, or
is pyrazolyl-$C_1$–$C_4$-alkyl, which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the pyrazole ring,
$R_p^3$ are one to five identical or different radicals from the group consisting of: hydrogen, halogen, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkoxyalkoxy, $C_1$–$C_6$-alkylcarbonyl;
n is 0–5;
p is, depending on the number of free valencies, 0–4.

2. A benzamidoxime of the formula I as claimed in claim 1 where A is phenyl.

3. A benzamidoxime of the formula I as claimed in claim 1 where A is pyridyl.

4. A benzamidoxime of the formula I as claimed in claim 1 where Y is a carbon.

5. A benzamidoxime of the formula I as claimed in claim 1 where $R_n^1$ are one to five identical or different radicals from the group consisting of: hydrogen, halogen, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkoxyalkoxy.

6. A benzamidoxime of the formula I as claimed in claim 1 where
$R^2$ is phenyl-$C_1$–$C_6$-alkyl, which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the phenyl ring, or
is thienyl-$C_1$–$C_4$-alkyl, which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the thienyl ring, or
is pyrazolyl-$C_1$–$C_4$-alkyl, which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the pyrazole ring.

7. A benzamidoxime of the formula I as claimed in claim 1 where $R_p^3$ are one or two identical or different radicals from the group consisting of: hydrogen, halogen, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkoxyalkoxy.

8. A benzamidoxime of the formula I as claimed in claim 7 where $R_p^3$ are hydrogen or $C_1$–$C_4$-alkyl.

9. A benzamidoxime of the formula I as claimed in claim 1 where:
A is an aryl or hetaryl radical from the group consisting of phenyl, pyridyl and thienyl;
Y is a carbon;
$R_n^1$ are one to five identical or different radicals from the group consisting of: hydrogen, halogen, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkoxyalkoxy;
$R^2$ is phenyl-$C_1$–$C_6$-alkyl, which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the phenyl ring, or
is thienyl-$C_1$–$C_4$-alkyl, which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the thienyl ring, or
is pyrazolyl-$C_1$–$C_4$-alkyl, which may carry one or more substituents selected from the group consisting of halogen, $C_1$–$C_4$-alkyl, $C_1$–$C_4$haloalkyl, $C_1$–$C_4$-alkoxy and $C_1$–$C_4$-haloalkoxy on the pyrazole ring,
$R_p^3$ are one or two identical or different radicals from the group consisting of: hydrogen, halogen, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkoxyalkyl;
n is 0–5;
p is 0–2.

10. A process for preparing the benzamidoxime derivatives of the formula I as claimed in claim 1, which comprises reacting benzonitriles of the formula II

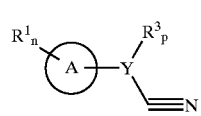

II with hydroxylamine or salts thereof in aqueous solution, preferably at a pH greater than 8, to give benzamidoximes of the formula III

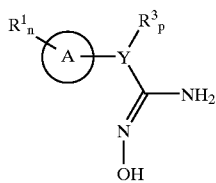

which are then alkylated using a cyclopropylmethyl halide to give benzamidoximes of the formula IV

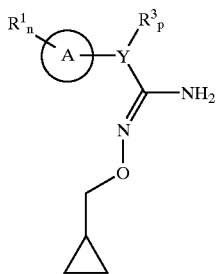

which are subsequently converted, using an appropriate acyl halide, into benzamidoxime derivatives of the formula I.

11. An agrochemical composition, comprising a fungicidally effective amount of at least one benzamidoxime derivative of the formula I as claimed in claim 1 and, if appropriate, agriculturally utilizable auxiliaries or additives.

12. A method for controlling harmful fungi, which comprises treating the harmful fungi, their habitat or the plants, areas, materials or spaces to be kept free from them with a fungicidally effective amount of a compound of the formula I or the fungicidal composition comprising a benzamidoxime derivative of the formula I as claimed in claim 11.

13. The benzamidoxime of formula I defined in claim 1, wherein A is phenyl and Y is carbon.

14. The benzamidoxime of formula I defined in claim 13, wherein $R^2$ is phenyl-$C_1$–$C_6$-alkyl, which optionally carries one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the phenyl ring.

15. The benzamidoxime of formula I defined in claim 13, wherein $R_p^3$ are hydrogen or $C_1$–$C_4$-alkyl.

16. The benzamidoxime of formula I defined in claim 13, wherein A is phenyl;

Y is a carbon;

$R_n^1$ are one to five identical or different radicals selected from the group consisting of: hydrogen, halogen, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkoxyalkoxy;

$R^2$ is phenylmethyl, wherein the phenyl ring optionally carries one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy;

$R_p^3$ is hydrogen or methyl;

n is 0–5; and p is 0–1.

\* \* \* \* \*